(12) United States Patent
Kim et al.

(10) Patent No.: US 7,738,104 B2
(45) Date of Patent: Jun. 15, 2010

(54) GAS SENSING APPARATUS AND METHOD OF SENSING GAS USING THE SAME

(75) Inventors: In-Gyoo Kim, Daejon (KR); Gyung-Ock Kim, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 214 days.

(21) Appl. No.: 12/111,864

(22) Filed: Apr. 29, 2008

(65) Prior Publication Data

US 2009/0153864 A1 Jun. 18, 2009

(30) Foreign Application Priority Data

Dec. 17, 2007 (KR) .................. 10-2007-0132315

(51) Int. Cl.
*G01N 21/00* (2006.01)
*G01J 5/02* (2006.01)
(52) U.S. Cl. .................. 356/437; 356/436; 250/339.13; 250/343
(58) Field of Classification Search ................ None
See application file for complete search history.

(56) References Cited

U.S. PATENT DOCUMENTS 3,098,932 A 7/1963 Laudon 4,934,816 A 6/1990 Silver et al.

FOREIGN PATENT DOCUMENTS

| DE | 102006031833 A1 | 12/2007 |
| EP | 1723407 B1 | 11/2007 |
| JP | 2006266771 A | 10/2006 |

OTHER PUBLICATIONS

D. Weidmann et al., "Development of a compact quantum cascade laser spectrometer for field measurements of $CO_2$ isotopes", Applied Physics, vol. B80, pp. 255-260, Sep. 29, 2005.
Joel A. Silver et al., "Carbon Monoxide Sensor for Combustion Feeback Control", $44^{th}$ AIAA Aerospace Sciences Meeting and Exhibit, Jan. 9-12, 2006, pp. 1-9, American Institute of Aeronautics and Astronautics, Inc., Reno, Nevada.

*Primary Examiner*—Gregory J Toatley, Jr.
*Assistant Examiner*—Amanda H Merlino

(57) ABSTRACT

Provided are a gas sensing apparatus and a gas sensing method using the apparatus. The gas sensing apparatus includes a detection chamber, a light source, a light sensor, a gas source, and a controller. The light source is disposed at one end of the detection chamber, and a light sensor is disposed at the other end of the detection chamber. The gas source provides gas to the detection chamber. The controller controls the light source and the light sensor. The light source includes a laser supplying laser light, and a light scanner reflecting and scanning the laser light in the detection chamber. The controller includes a phase sensitive detector electrically connected to the light sensor.

12 Claims, 5 Drawing Sheets

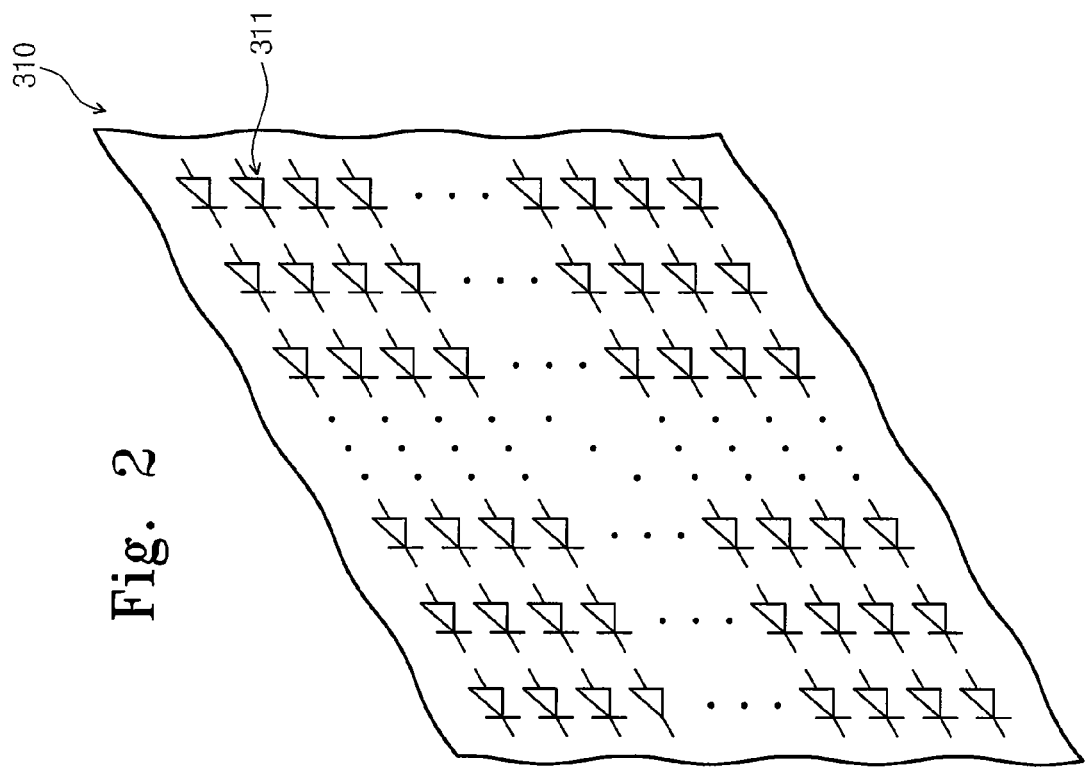
Fig. 2
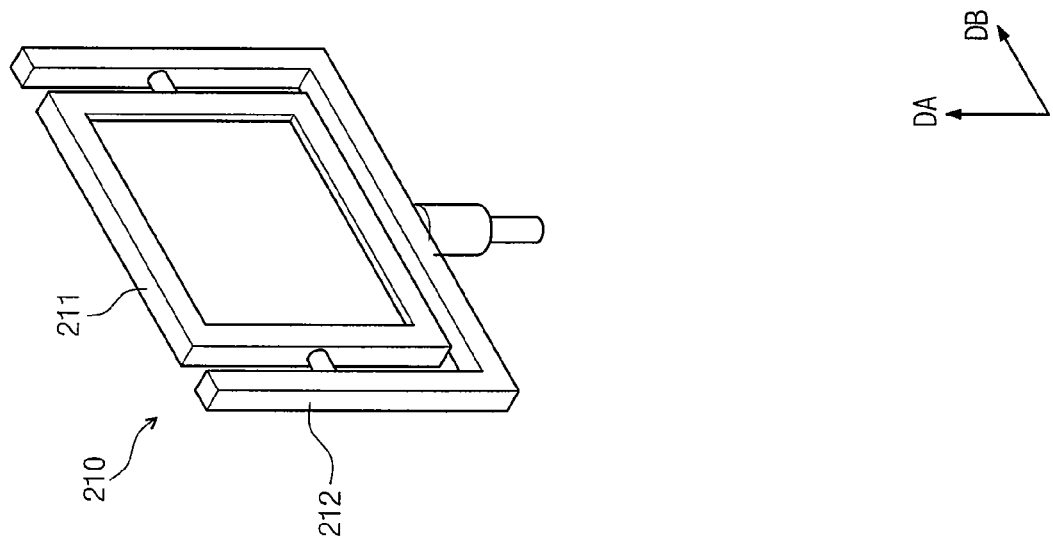

GAS SENSING APPARATUS AND METHOD OF SENSING GAS USING THE SAME

CROSS-REFERENCE TO RELATED APPLICATIONS

This U.S. non-provisional patent application claims priority under 35 U.S.C. §119 of Korean Patent Application No. 10-2007-0132315, filed on Dec. 17, 2007, the entire contents of which are hereby incorporated by reference.

BACKGROUND OF THE INVENTION

The present invention disclosed herein relates to a gas sensing apparatus, and more particularly, to a light absorption-type gas sensing apparatus and a method of sensing gas using the gas sensing apparatus.

Energy wavelengths corresponding to kinetic modes of gas molecules to be detected in environmental pollutant measuring, process gas monitoring, toxic gas detection, etc. are largely concentrated within the mid-infrared spectrum. Spectroscopic methods currently in use or under development typically employ thermo-resistive light sources or mid-infrared lasers. Particularly, when lasers are used, ultra-low concentrations of gas below one part per billion (ppb) can be detected, allowing for remote gas detection. Thus, research in the field of laser detection is vigorously being pursued.

For detecting highly-diluted gas with high sensitivity using detection chambers, an important point is for laser light to provide coverage broad enough to yield an adequate light absorption signal when contacting gas molecules. For this end, a method of lengthening the light beam path with multi-reflection, achieved by mounting mirrors within a detection chamber such as a white chamber, is widely used. However, this method has the limitation in that light intensity is reduced when reflected multiple times. Limiting the decrease in light intensity by reducing the number of times the light is reflected necessitates substantially increasing the length and volume of the chamber.

SUMMARY OF THE INVENTION

The present invention provides a gas sensing apparatus that is small in size and has low power consumption, yet is capable of highly sensitive gas detection.

The present invention also provides a method of sensing gas using the above gas sensing apparatus.

Embodiments of the present invention provide apparatuses for sensing gas including: a detection chamber; a light source disposed at one end of the detection chamber, and a light sensor disposed at the other end of the detection chamber; a gas source providing gas to the detection chamber; and a controller controlling the light source and the light sensor, wherein the light source includes a laser supplying laser light, and a light scanner reflecting and scanning the laser light in the detection chamber, and the controller includes a phase sensitive detector electrically connected to the light sensor.

In some embodiments, the light source may further include a scanner driver oscillating the light scanner, the scanner driver providing an oscillation frequency to the light scanner. The light scanner may include a micro-mirror, and a oscillation support supporting the micro-mirror, and the oscillation support may oscillate the micro-mirror in one direction or in two mutually intersecting directions, through the oscillation frequency. The micro-mirror may scan the reflected laser light one-dimensionally or two-dimensionally. The phase sensitive detector may be electrically connected to the scanner driver and may designate the oscillation frequency as a reference frequency.

In other embodiments, the light sensor may include a sensor array absorbing light provided by the light source and passing through the detection chamber, and a sensor driver driving the sensor array. The sensor array may include sensors arranged in two mutually intersecting directions.

In still other embodiments, the controller may include a computer electrically connected to the phase sensitive detector to process data obtained through the phase sensitive detector.

In other embodiments of the present invention, methods for sensing gas include: providing a detection chamber; providing gas to the detection chamber; scanning light in the detection chamber; absorbing the scanned light; and obtaining volumetric data of the gas from the absorbed light.

In some embodiments, scanning the light in the detection chamber may include providing a micro-mirror at one side of the detection chamber, providing laser light to the micro-mirror, and oscillating the micro-mirror. The micro-mirror may be oscillated by an oscillation frequency provided to a oscillation support supporting the micro-mirror, and the oscillation support may oscillate the micro-mirror in one direction or two mutually intersecting directions. Obtaining the volumetric data of the gas may include converting the absorbed light to an electrical signal, and providing the electrical signal to a phase sensitive detector. The phase sensitive detector may designate the oscillation frequency as a reference frequency.

According to present embodiments, laser light can be scanned through the oscillation of a micro-mirror provided in a detection chamber. Thus, the sectional dispersion of light that scans gas molecules to be detected in the detection chamber can be widened. Accordingly, laser light can be efficiently used without lengthening the detection chamber, and gas detection within the chamber can easily be performed.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures:

FIG. 2 is a schematic view of a light scanner and sensor array of a gas sensing apparatus according to an embodiment of the present invention.

DETAILED DESCRIPTION OF PREFERRED EMBODIMENTS

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

In the figures, the dimensions of elements and the relative dimensions of elements may be exaggerated for clarity of illustration.

Hereinafter, an exemplary embodiment of the present invention will be described with the accompanying drawings.

Figure 1:
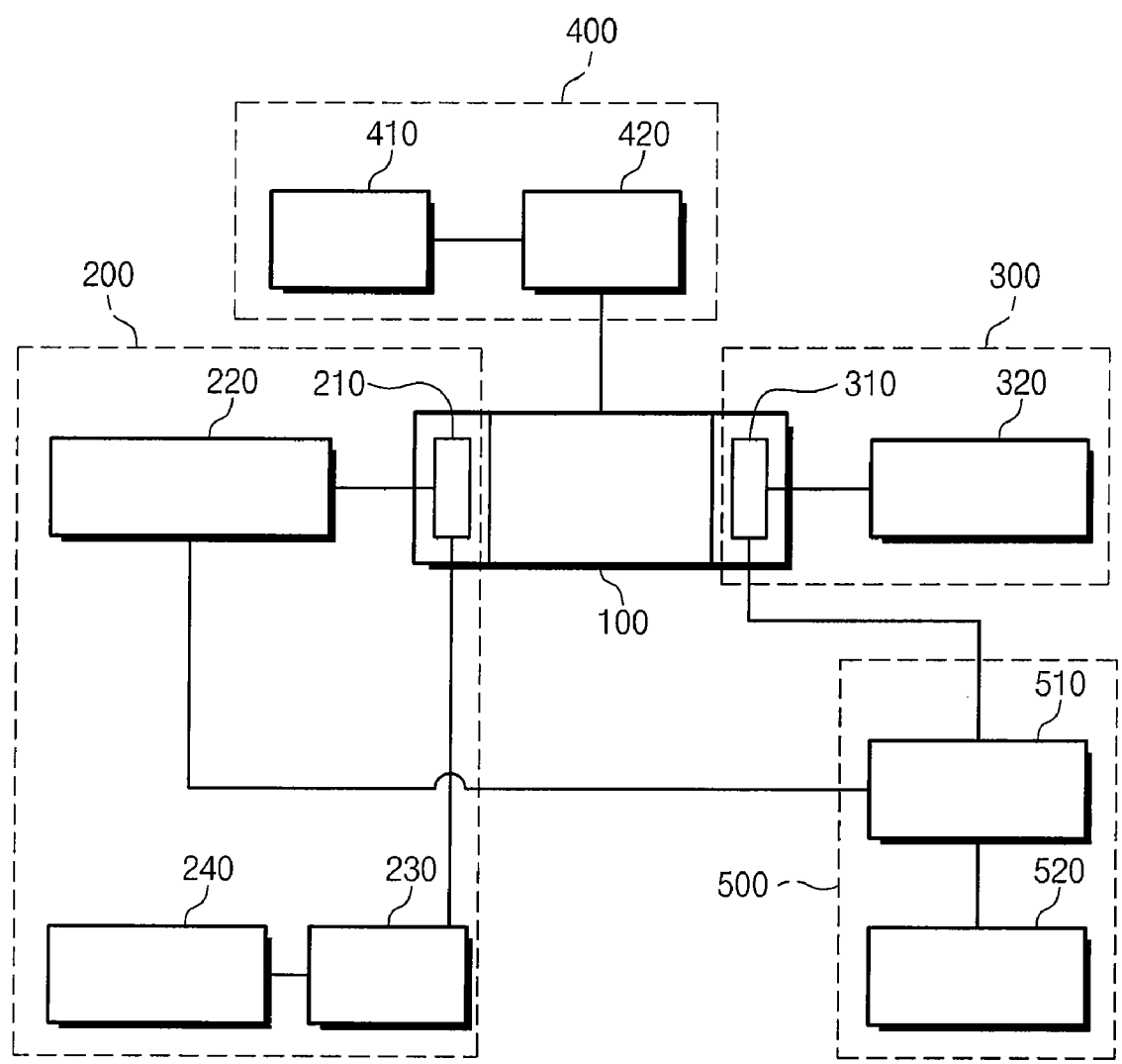
FIG. 1 is a block diagram of a gas sensing apparatus according to an embodiment of the present invention.

Referring to FIG. 1, a gas sensing apparatus according to an embodiment of the present invention will be described. The gas sensing apparatus includes a detection chamber 100, a light source 200, a light sensor 300, a gas source 400, and a controller 500. The light source 200 may include a light scanner 210, a scanner driver 220, a laser 230, and a laser driver 240. The light sensor 300 may include a sensor array 310 and a sensor driver 320. The gas source 400 may include a gas container 410 and a gas flow regulator 420. The controller 500 may include a phase sensitive detector 510 and a computer 520. The phase sensitive detector 510 may be, for example, a lock-in amplifier.

Referring to FIG. 2, a light scanner 210 and sensor array 310 according to an embodiment of the present invention will be described. The light scanner 210 may include a micro-mirror 211 and a oscillation support 212. A metal coating layer may be formed on the reflective surface of the micro-mirror 211. The metal coating layer may, for example, include a metal material and have a high reflectance of mid-infrared wavelengths. The oscillation support 212 supports the micro-mirror 211, and may have torsional tolerance. The sensor array 310 may include a plurality of sensors 311. The sensors 311 may be optical diodes that absorb light. The plurality of sensors 311 may be arranged in a first direction (DA) and/or a second direction (DB).

Referring again to FIGS. 1 and 2, the light scanner 210 and sensor array 310 are disposed at either end of the detection chamber 100. FIG. 2 is a schematic view of a light scanner and sensor array of a gas sensing apparatus according to an embodiment of the present invention. The scanner driver 220 may be electrically connected to the light scanner 210, to drive the light scanner 210. For example, the scanner driver 220 may generate a predetermined oscillation frequency, and the light scanner 210 may be oscillated by the scanner driver 220 at a speed of about several kHz to several MHz and an oscillation angle of about several to several tens of degrees. The oscillation support 212 may employ electro-static force to oscillate the micro-mirror 211 in uni-directional or bi-directional rotation. For example, the oscillation support 212 may oscillate the micro-mirror 211 in the first direction (DA) and/or the second direction (DB). The laser driver 240 may supply pulse or direct current power to the laser 230, and the laser 230 that receives the power may provide laser light to the micro-mirror 211 of the light scanner 210. The micro-mirror 211 may reflect the laser light to be scanned through the detection chamber by the sensor array, and the reflected light may be scanned through oscillation in one dimension—for example, in the first direction (DA) or the second direction (DB), or in two dimensions.

The gas source 400 supplies gas stored in the gas container 410 to the detection chamber 100. The gas flow regulator 420 controls the flow of gas supplied to the detection chamber 100. The reflected light that is scanned passes through the gas provided in the detection chamber 100, and is absorbed by the sensor array 310. The sensor array 310 is operated by the sensor driver 320. For example, the sensor driver 320 may convert a light signal absorbed by the sensor array 310 to an electrical signal, and amplify the electrical signal. Also, the sensor driver 320 may provide the amplified electrical signal to the phase sensitive detector 510 of the controller 500.

The phase sensitive detector 510 may be electrically connected to the scanner driver 220 and the sensor array 310, respectively. The phase sensitive detector 510 may designate an oscillation frequency generated by the scanner driver 220 as a reference frequency. The phase sensitive detector 510 may revise a signal-to-noise ratio (S/N) in proportion to a square root of the reference frequency. Accordingly, a superior signal can be obtained than one derived by modulating a chopper or electro-optic modulator laser light and using the modulated frequency as a reference frequency.

Data on the inside of the detection chamber may be obtained from the light signal (or electrical signal converted from the light signal) by the phase sensitive detector 510 through the reflected light scanned by the sensor array 310. The computer 520 may be electrically connected to the phase sensitive detector 510 to control the phase sensitive detector 510, and process data obtained through the phase sensitive detector 510 and display the data through a display unit.

Referring to FIGS. 1, and 3 through 5, a method for sensing gas according to embodiments of the present invention will be described.

Figure 3:
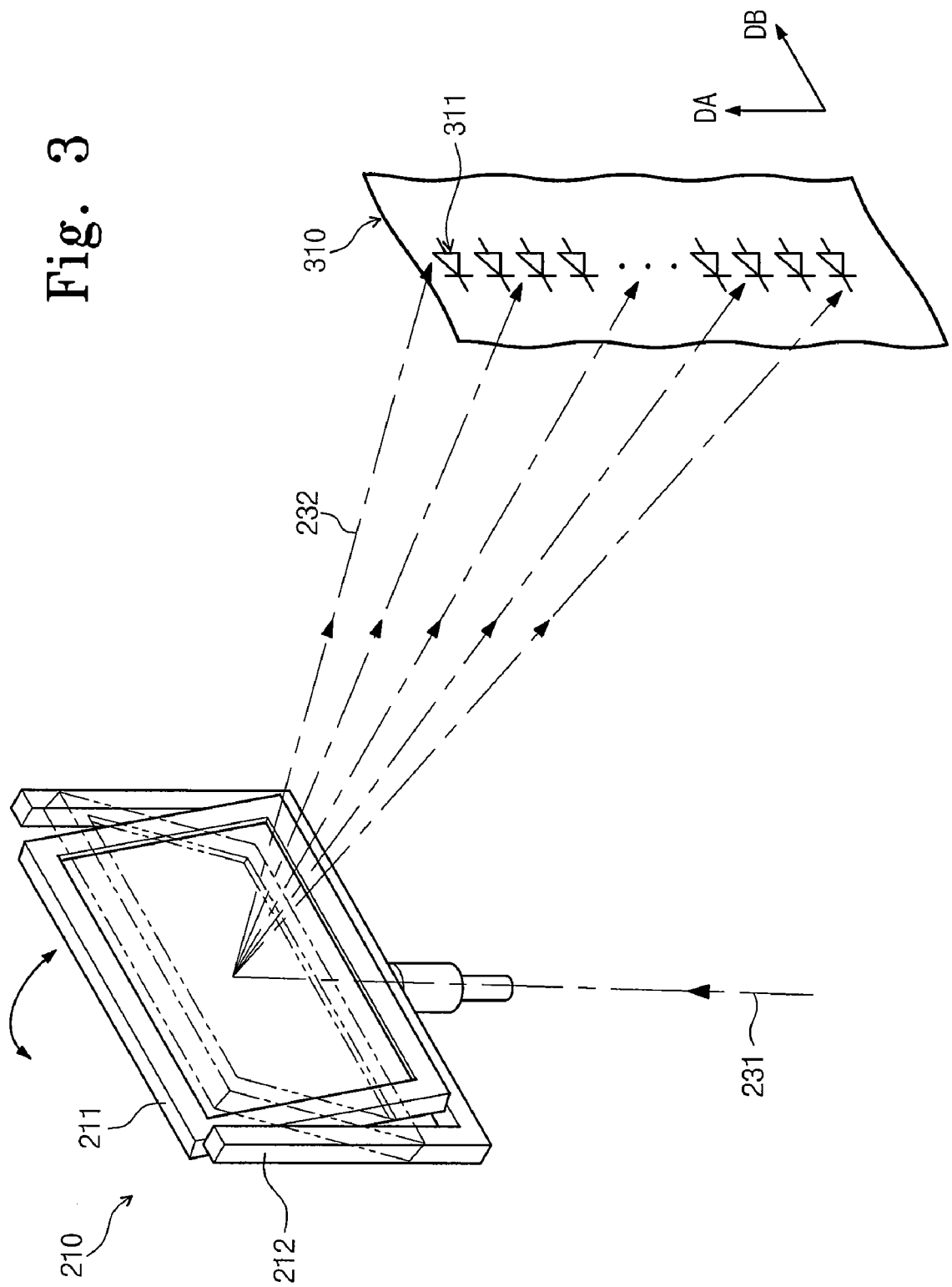
FIGS. 3 through 5 are diagrams illustrating a gas sensing method according to embodiments of the present invention.

Referring to FIGS. 1 and 3, the gas source 400 supplies gas to the detection chamber 100. The gas flow regulator 420 may control the flow of the gas supplied from the gas compartment 410 to the detection chamber 100. The laser 230 that receives pulse or direct current power from the laser driver 240 supplies a laser light 231 to the micro-mirror 211 of the light scanner 210. The micro-mirror 211 reflects the laser light 231 and supplies reflected light 232 to the detection chamber 100. Here, the scanner driver 220 may provide an oscillation frequency to the oscillation support 212, and the phase sensitive detector 510 may designate the oscillation frequency as a reference frequency. The swivel support 212 may oscillate the micro-mirror 211 in one direction, for example, the first direction (DA), by means of the oscillation frequency. The reflected light 232 may be scanned in the first direction (DA) through the oscillation of the micro-mirror 211.

The scanned reflected light 232 passes through the detection chamber and is absorbed by the sensors 311 arranged in the first direction (DA) on the sensor array 310. The sensors 311 may absorb the reflected light 232 scanned in the first direction (DA). The sensor array 310 may be driven by the sensor driver 320, and the light signal of the absorbed reflected light is supplied to the phase sensitive detector 510. The phase sensitive detector 510 may be controlled by the computer 520 to obtain data on the inside of the detection chamber from the light signal—for example, data on the spatial distribution of gas within the detection chamber. The data may be processed by the computer 520, and may be displayed on the display unit of the computer 520.

Figure 4:
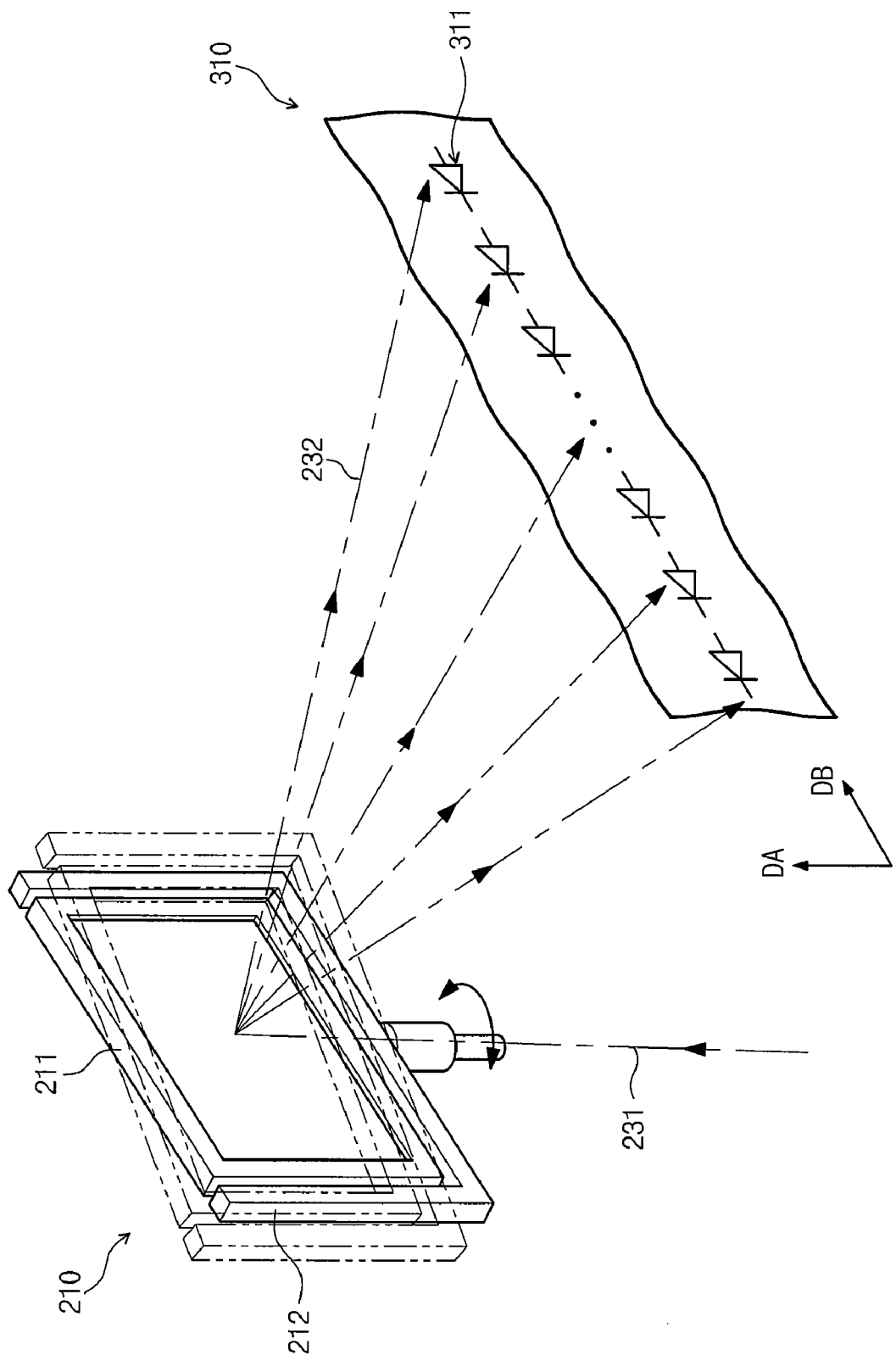
Figure 5:
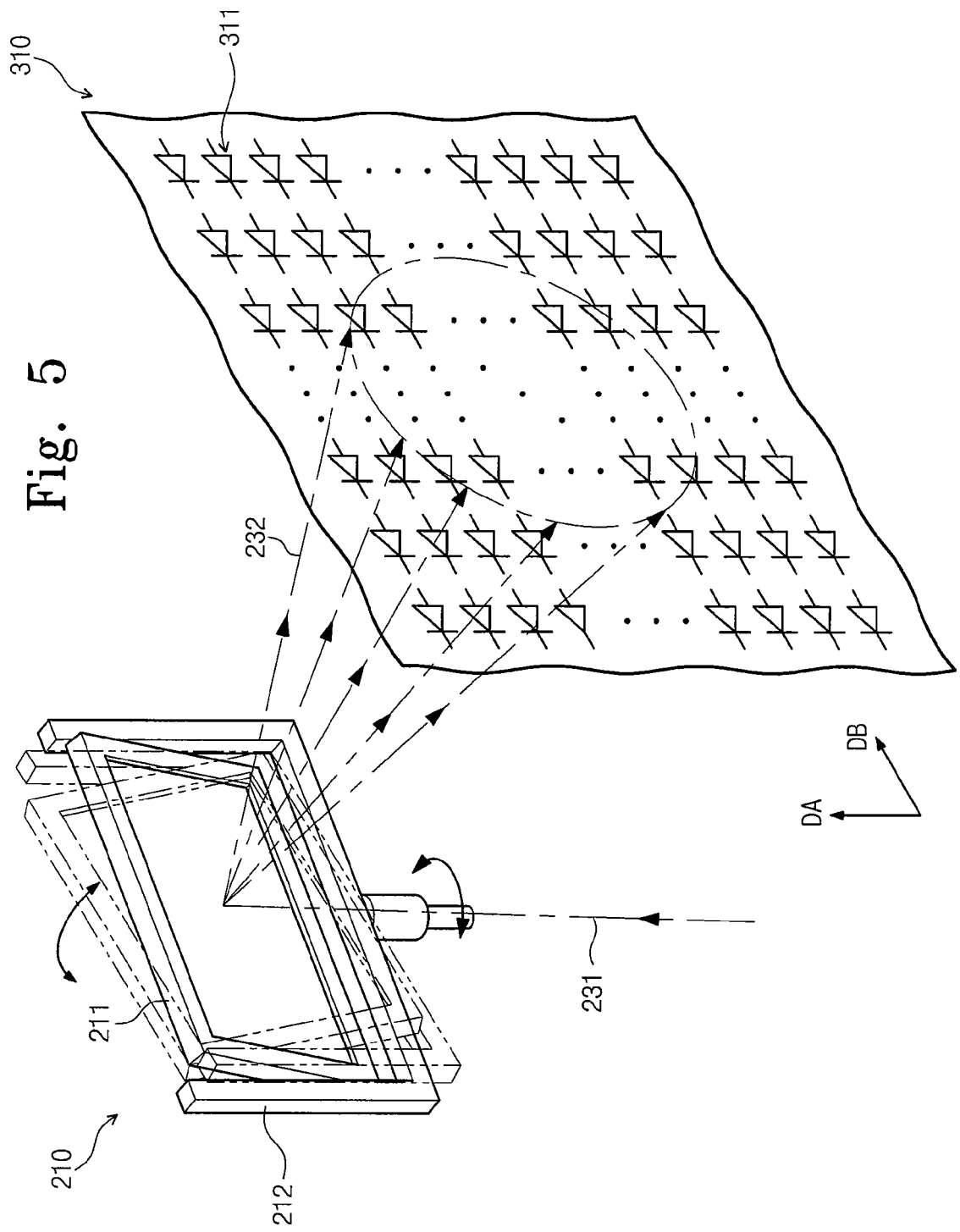

Through the oscillation of the swivel support 212, the micro-mirror 211 may oscillate in various directions. Referring to FIGS. 1 and 4, the oscillation support 212 may oscillate the micro-mirror 211 in the second direction (DB). The reflected light 232 may be scanned in the second direction (DB) through the oscillation of the micro-mirror 211. Also, referring to FIGS. 1 and 5, the oscillation support 212 may oscillate the micro-mirror 211 bi-directionally. For example, the oscillation support 212 may oscillate the micro-mirror 211 bi-directionally in both the first direction (DA) and the second direction (DB). Through the oscillation of the micro-mirror 211, the reflected light may be scanned two-dimensionally. However, because selected oscillation directions may be varied, oscillation directions of the present invention should therefore not be restricted. Also, even if the reflected light 232 is scanned in one dimension by a uni-directional oscillation of the micro-mirror 211, the sensors 311 may be arranged in both the first direction (DA) and the second direction (DB).

According to embodiments of the present invention, because laser light 231 is scanned through oscillation of the micro-mirror 211 and provided to the detection chamber 100, the sectional area of reflected light 232 scattered by molecules of gas to be detected within the detection chamber 100 can be broadened. Thus, laser light can efficiently be employed without lengthening the detection chamber 100, and detection of gas within the detection chamber 100 can easily be performed.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An apparatus for sensing gas, comprising:
    a detection chamber;
    a light source disposed at one end of the detection chamber, and a light sensor disposed at the other end of the detection chamber;
    a gas source providing gas to the detection chamber; and
    a controller controlling the light source and the light sensor,
    wherein the light source includes a laser supplying laser light, and a light scanner reflecting and scanning the laser light in the detection chamber, and
    the controller includes a phase sensitive detector electrically connected to the light sensor.

2. The apparatus of claim 1, wherein the light source further includes a scanner driver oscillating the light scanner, the scanner driver providing an oscillation frequency to the light scanner.

3. The apparatus of claim 2, wherein the light scanner comprises:
    a micro-mirror; and
    a oscillation support supporting the micro-mirror,
    wherein the oscillation support oscillates the micro-mirror in one direction or in two mutually intersecting directions, through the oscillation frequency.

4. The apparatus of claim 3, wherein the micro-mirror scans the reflected laser light one-dimensionally or two-dimensionally.

5. The apparatus of claim 2, wherein the phase sensitive detector is electrically connected to the scanner driver and designates the oscillation frequency as a reference frequency.

6. The apparatus of claim 1, wherein the light sensor comprises:
    a sensor array absorbing light provided by the light source and passing through the detection chamber; and
    a sensor driver driving the sensor array.

7. The apparatus of claim 6, wherein the sensor array comprises sensors arranged in two mutually intersecting directions.

8. The apparatus of claim 1, wherein the controller comprises a computer electrically connected to the phase sensitive detector to process data obtained through the phase sensitive detector.

9. A method for sensing gas, comprising:
    providing a detection chamber;
    providing gas to the detection chamber;
    scanning light in the detection chamber;
    absorbing the scanned light; and
    obtaining volumetric data of the gas from the absorbed light.

10. The method of claim 9, wherein scanning the light in the detection chamber comprises:
    providing a micro-mirror at one side of the detection chamber;
    providing laser light to the micro-mirror; and
    oscillating the micro-mirror.

11. The method of claim 10, wherein the micro-mirror is oscillated by an oscillation frequency provided to a oscillation support supporting the micro-mirror, and the oscillation support oscillates the micro-mirror in one direction or two mutually intersecting directions.

12. The method of claim 11, wherein obtaining the volumetric data of the gas comprises:
    converting the absorbed light to an electrical signal; and
    providing the electrical signal to a phase sensitive detector,
    wherein the phase sensitive detector designates the oscillation frequency as a reference frequency.

* * * * *